United States Patent [19]

Hacker et al.

[11] Patent Number: 4,760,013

[45] Date of Patent: Jul. 26, 1988

[54] SULFONIUM SALT PHOTOINITIATORS

[75] Inventors: Nigel P. Hacker, Morgan Hill; Carl E. Larson, San Jose, both of Calif.

[73] Assignee: International Business Machines Corporation, Armonk, N.Y.

[21] Appl. No.: 15,402

[22] Filed: Feb. 17, 1987

[51] Int. Cl.⁴ .................... G03C 5/04; G03C 1/68; C07F 9/90; C08F 8/18
[52] U.S. Cl. ........................ 430/280; 568/57; 568/58; 522/31; 430/914; 430/921; 430/270
[58] Field of Search ............ 568/57, 58; 430/280, 430/914, 921; 522/31

[56] References Cited

U.S. PATENT DOCUMENTS

| | | | |
|---|---|---|---|
| 4,102,687 | 7/1978 | Crivello | 96/115 R |
| 4,156,035 | 5/1979 | Tsao et al. | 430/281 X |
| 4,173,476 | 11/1979 | Smith et al. | 430/145 X |
| 4,256,828 | 3/1981 | Smith | 430/914 X |
| 4,537,854 | 8/1985 | Crivello | 430/921 X |

Primary Examiner—Paul R. Michl
Assistant Examiner—Cynthia Hamilton
Attorney, Agent, or Firm—Joseph G. Walsh

[57] ABSTRACT

Alkyldiarylsulfonium salts of 9, 10,-dithiophenoxyanthracene are useful as photoinitiators in resist compositions, such as epoxy resin formulations, particularly using long wavelength light.

7 Claims, No Drawings

SULFONIUM SALT PHOTOINITIATORS

DESCRIPTION

1. Technical Field

The present invention is concerned with novel compounds useful as photoinitiators, particularly when long wavelength light is used.

2. BACKGROUND ART

Sulfonium salts have been known as photoinitiators in the past. See for example U.S. Pat. Nos. 4,102,687 and 4,537,854, both of which show sulfonium salt photoinitiators having some structural similarity to the present invention, but also having obvious structural differences.

The prior art has emphasized the use of triarylsulfonium salts, which have both thermal stability and thermal activity. In contrast, alkylsulfonium salts are considered not to be useful due to poor thermal stability and low ultraviolet absorbence. The two major drawbacks to use of triarylsulfonium salts are the poor photospeeds (about 500 mJ) at accessible wavelengths (greater than 350 mn) for production tools and the relatively large amounts of initiator required (up to 10% weight).

DISCLOSURE OF THE PRESENT INVENTION

The present invention is concerned with novel alkyldiarylsulfonium salts derived from 9,10-dithiophenoxyanthracene. The compounds have cations with the formula:

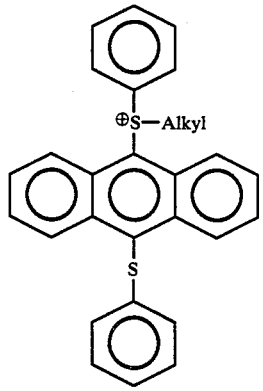

The anions of the salts preferred for use as photoinitiators are, in general, those containing halogen and a metal or metaloid atom, for example, $SbF_6^-$, $AsF_6^-$, $BF_4^-$ and $PF_6^-$. The alkyl group is preferably a lower alkyl group, such as ethyl or ethyl.

The addition of these novel salts to organic resins greatly reduce the required exposure time for development. These new compounds are far superior to triarylsulfonium salts as photoinitiators.

The novel compounds are used in conjunction with organic resins, particularly those susceptible to cationic initiation. The most preferred resins are epoxy resins.

It is of particular advantage of the compounds of the present invention that they are thermally stable and are also effective at low concentrations even in the absence of initiators. In general, concentrations as low as about 0.5% are preferred. In contrast, most commercially available onium salts are used as photoinitiators in concentrations from about 3-10 weight %.

A typical preferred compound of the present invention is ethylphenyl-(9-thiophenoxyanthracenyl-10) sulfonium hexafluoroantimonate ($EPTAS.SbF_6$). This compound is thermally stable but it decomposes photochemically. A solution of the compound in acetonitrile was heated to 70 degrees C. for two hours and showed no change in its ultraviolet absorption spectrum after thermolysis. Furthermore, $EPTAS.SbF_6$ did not cause crosslinking of an epoxy resin after heating at 100 degrees C. for six hours. On the other hand, irradiation of the same material in dichloromethane solution resulted in bleaching.

EXAMPLES

Synthesis of 9,10-dithiophenoxyantracene (DTPA)

Potassium hydroxide (19.6 g) and thiophenol (35.5 ml) were heated at 170 degrees C. in dimethylacetamide for two hours. 9,10-dibromoanthracene (37.5 g) was added and the mixture heated at 170 degrees C. an additional two hours. (The corresponding dichloro compound has also been used successfully.) The mixture was quenched with water and the precipitate recrystallized from chloroform/ethanol to give DTPA.

Synthesis of Ethylphenyl-(9-thiophenoxyanthracenyl-10)sulfonium hexafluoroantimonate ($EPTAS.SbF_6$)

DTPA (1 g), ethyliodide (0.5 ml) and silver hexafluoroantimonate (2 g) in dichloromethane were stirred at ambient temperature for two days. The mixture was filtered and the solution evaporated to leave a yellow solid which was recrystallized from dichloromethane/ether.

Our experiments were carried out using an epoxy resin system containing 85 wt % Epirez SU8 (Trademark of Celanese Corporation) and 15 wt % CY179 (Trademark of Ciba-Geigy Corporation). The initiator systems used were 5.0% wt triarylsulfonium salt photoinitiator (ASP), 0.5% wt ASP, 3.0% wt ASP and 0.5% wt DTPA, 0.5% wt ASP and 0.5% wt DTPA or 0.5% wt $EPTAS.SbF_6$.

Synthesis of Methylphenyl-(9-thiophenoxyanthracenyl)-10)sulfonium hexafluoroantimonate (MEPTAS)

DTPA (1 g), methyliodide (0.25 ml) and silver hexafluoroantimonate (1.2 g) were sonicated for 18 hours. The mixture was filtered and the solution purified by chromatography and recrystallized from dichloromethane/ether to give $MEPTAS.SbF_6$ as a yellow solid.

Representative epoxy films (typically 2 mils thick) containing varying initiator/sensitizer amounts were coated. The films were laminated to small coupons and taken through a standard processing cycle. The process is as follows: (1) lamination to coupons at 70 degrees C., (2) exposure of film through artwork, (3) post bake at 70 degrees C. for two minutes, (4) spray development in 1,1,1-trichloroethane for 1 minute, and (5) air dry and inspect pattern. The exposures (500 W Hg/Xenon lamp) were made through a quartz neutral density step wedge.

The photospeeds were as follows:

| Initiator System | Photospeed (mJ/sq. cm.) |
|---|---|
| 5.0% wt ASP (triarylsulfonium salt photoinitiator) | 80 |
| 0.5% wt ASP | 500 |
| 0.5% wt ASP + 0.5% wt DTPA | 500 |
| 0.5% wt EPTAS.SbF$_6$ | 15 |

It is thus seen that the alkyldiarylsulfonium salt of the present invention was over five times faster than a typical triaryl compound, when present at one-tenth of the concentration of the triaryl compound.

What is claimed is:

1. Alkyldiarylsulfonium salts of 9,10-dithiophenoxyanthracene.
2. Ethylphenyl-(9-thiophenoxyanthracenyl-10)sulfonium hexafluoroantimonate.
3. Ethylphenyl-(9-thiophenoxyanthracenyl-10)sulfonium tetrafluoroborate.
4. Methylphenyl-(9-thiophenoxyanthracenyl-10)sulfonium hexafluoroantimonate.
5. Methylphenyl-(9-thiophenoxyanthracenyl-10)sulfonium tetrafluoroborate.
6. A resist composition comprising an organic resin and of a photoinitiator which is a compound claimed in claim 1 in an amount effective for ultraviolet curing.
7. A resist composition as claimed in claim 6 wherein the resin is an epoxy resin.

* * * * *